US00PP17530P2

(12) United States Plant Patent

Eskelund Hansen

(10) Patent No.: US PP17,530 P2
(45) Date of Patent: Mar. 27, 2007

(54) ROSE PLANT NAMED 'EVERA 131'

(50) Latin Name: *Rosa hybrida*
Varietal Denomination: Evera 131

(76) Inventor: Rosa Eskelund Hansen, Fiskervænget 9, 5600, Fåborg (DK)

( * ) Notice: Subject to any disclaimer, the term of this patent is extended or adjusted under 35 U.S.C. 154(b) by 0 days.

(21) Appl. No.: 11/204,333

(22) Filed: Aug. 15, 2005

(51) Int. Cl.
*A01H 5/00* (2006.01)

(52) U.S. Cl. ..... Plt./120

(58) Field of Classification Search ..... Plt./120, Plt./121
See application file for complete search history.

*Primary Examiner*—Kent Bell
(74) *Attorney, Agent, or Firm*—C. A. Whealy

(57) ABSTRACT

A new and distinct cultivar of rose plant named 'Evera 131', characterized by its upright, compact, uniform and rounded plant habit; dark green-colored leaves; double salmon pink-colored flowers; flowers held upright on strong and erect peduncles; and good postproduction longevity.

1 Drawing Sheet

Botanical designation: *Rosa hybrida.*
Cultivar denomination: 'Evera 131'.

BACKGROUND OF THE INVENTION

The present invention relates to a new and distinct cultivar of the Rose class, botanically known as *Rosa hybrida,* commercially known as a potted Rose and hereinafter referred to by the name 'Evera 131'.

The new Rose plant is a product of a planned breeding program conducted by the Inventor in Denmark. The objective of the breeding program was to develop new potted Rose cultivars with novel and attractive flower colors, disease resistance and excellent postproduction longevity.

The new Rose plant originated from a cross-pollination made by the Inventor on Jun. 1, 2002 of two unnamed proprietary *Rosa hybrida* seedlings, not patented. The cultivar Evera 131 was discovered and selected by the Inventor as a flowering plant within the progeny of the stated cross-pollination in a controlled environment in Denmark. Plants of the new cultivar differ primarily from plants of the parent selections primarily in flower color and plant shape.

Asexual reproduction of the new Rose plant by cuttings in Denmark since Feb. 1, 2004, has shown that the unique features of this new Rose plant are stable and reproduced true to type in successive generations of asexual reproduction.

SUMMARY OF THE INVENTION

The new Rose plant has not been observed under all possible environmental conditions. The phenotype may vary significantly with variations in environment such as temperature and light level, without, however, any variance in genotype.

The following traits have been repeatedly observed and are determined to be the unique characteristics of 'Evera 131'. These characteristics in combination distinguish the new Rose plant as a new and distinct cultivar.

1. Upright, compact, rounded and uniform plant habit.
2. Dark green-colored leaves.
3. Double salmon pink-colored flowers.

4. Flowers held upright on strong and erect peduncles.
5. Good postproduction longevity.

Plants of the new Rose plant can be compared to plants of the Rose cultivar Remoever, not patented. In side-by-side comparisons conducted in Denmark, plants of the new Rose differed from plants of the cultivar Remoever in the following characteristics:

1. Plants of the new Rose were not as cylindrical as plants of the cultivar Remoever.
2. Plants of the new Rose had smaller thorns than plants of the cultivar Remoever.
3. Plants of the new Rose had smaller flowers than plants of the cultivar Remoever.
4. Flowers of plants of the new Rose had many more petals per flower than flowers of plants of the cultivar Remoever.

BRIEF DESCRIPTION OF PHOTOGRAPHS

The accompanying colored photographs illustrate typical specimens of the vegetative growth and flowers of the new Rose plant, showing the colors as true as it is reasonably possible to obtain in colored reproductions of this type. Colors in the photographs may differ slightly from the color values cited in the detailed botanical description which accurately describe the actual colors of the new Rose plant.

The photograph at the top of the sheet comprises a side perspective view of four typical plants of the new Rose plant grown in a container in Denmark.

The photograph at the bottom of the sheet comprises a close-up view of four typical plants of the new Rose grown in a container.

DETAILED BOTANICAL DESCRIPTION

The following observations and measurements describe plants grown in Denmark during the summer in 10.5-cm containers in a glass greenhouse and under conditions which closely approximate commercial production conditions during the summer. Plants used for the description were single plants that were about four months old. In the following description, color references are made to The Royal Horticultural Society Colour Chart, 1995 Edition, except where general terms of ordinary dictionary significance are used.

Botanical classification: *Rosa hybrida* cultivar Evera 131.
Commercial classification: Potted Rose.
Parentage:
*Female, or seed, parent.*—Unnamed proprietary seedling, not patented.
*Male, or pollen, parent.*—Unnamed proprietary seedling, not patented.
Propagation:
*Type.*—Terminal or stem cuttings.
*Time to rooting.*—8 to 10 days with soil temperatures of 20° C.
*Root description.*—Fine; freely branching.
Plant description:
*Form.*—Upright, compact, uniform and rounded plant habit.
*Plant height.*—About 24 cm.
*Plant width.*—About 18 cm.
*Growth habit.*—Moderately vigorous; suitable for 10 to 12-cm containers.
*Stem description.*—Branching habit: About four lateral branches per plant. Lateral branch length: About 19 to 22 cm. Lateral branch diameter: About 4 mm. Internode length: About 2.5 cm. Texture: Smooth, glabrous. Color: Close to 143A. Thorns: Length: About 2 mm. Diameter: About 3 mm. Shape: Roughly deltoid. Color: 143A to 143B.
*Foliage description.*—Arrangement: Alternately; compound with typically three to five leaflets per leaf, generally symmetrical. Leaflet length: About 2.4 to 4.2 cm. Leaflet width: About 1.4 to 2.7 cm. Shape: Ovate. Apex: Acuminate. Base: Obtuse. Margin: Serrulate. Venation pattern: Pinnate; reticulate. Texture, upper and lower surfaces: Smooth, glabrous; leathery. Petiole length: About 1.2 to 2 cm. Petiole diameter: About 1 mm. Color: Developing foliage, upper surface: Between 137B and 137C. Developing foliage, lower surface: 138B. Fully expanded foliage, upper surface: 147A. Fully expanded foliage, lower surface: 138A. Venation, upper surface: 144A. Venation, lower surface: 144C. Petiole, upper and lower surfaces: 143A to 143B.
Flower description:
*Flower type and habit.*—Double salmon pink-colored flowers. Consistently symmetrical rosette flowers. Flowers borne singly on erect and strong peduncles; about four flower buds and flowers per plant. Flowers persistent.
*Flowering season.*—Year-round under greenhouse conditions, optimal flowering from spring through autumn under garden conditions; flower intermittent.
*Flower diameter.*—About 3.5 cm.
*Flower depth* (*height*).—About 2.5 cm.
*Flower longevity on plant.*—About two weeks.
*Fragrance.*—None detected.
*Flower buds.*—Shape: Ovoid. Length: About 1 to 1.5 cm. Diameter: About 9 to 12 mm. Color: 143C.
*Petals.*—Quantity: About 110 per flower. Length: About 1.5 to 2.8 cm. Width: About 1.1 to 3.1 cm. Shape: Broadly obovate. Apex: Rounded. Base: Obtuse. Margin: Entire. Texture, upper and lower surfaces: Smooth, glabrous; satiny. Color: When opening, upper surface: 15B. When opening, lower surface: 28C. Fully opened, upper surface: Towards the apex, 36B; towards the base, 21B. Fully opened, lower surface: Towards the apex, 38C; towards the base, 29B.
*Sepals.*—Quantity flower: Typically five. Calyx length: About 2.8 cm. Calyx diameter: About 6 mm. Shape: Linear; falcate. Apex: Sharply pointed. Base: Fused. Texture, upper and lower surfaces: Pubescent. Color, upper and lower surfaces: Close to 146A.
*Peduncles.*—Strength: Strong, but flexible. Aspect: Mostly erect. Length: About 3.2 to 4.5 cm. Diameter: About 3 mm. Texture: Smooth, glabrous. Color: 144A.
*Reproductive organs.*—Stamens: Quantity: About 65 per flower. Anther length: About 2 mm. Anther shape: Oval. Anther color: 14A. Pistils: Quantity: About 60 per flower. Pistil length: About 6 to 9 mm. Stigma color: 13B. Style color: 43A.
*Seed/fruit.*—Seed and fruit production has not been observed.
Disease/pest resistance: Plants of the new Rose have not been shown to be resistant to pathogens and pests common to Rose plants.
Temperature tolerance: Plants of the new rose have been shown to be tolerant to temperatures from 0 to 45° C.
It is claimed:
1. A new and distinct rose plant named 'Evera 131', as illustrated and described.

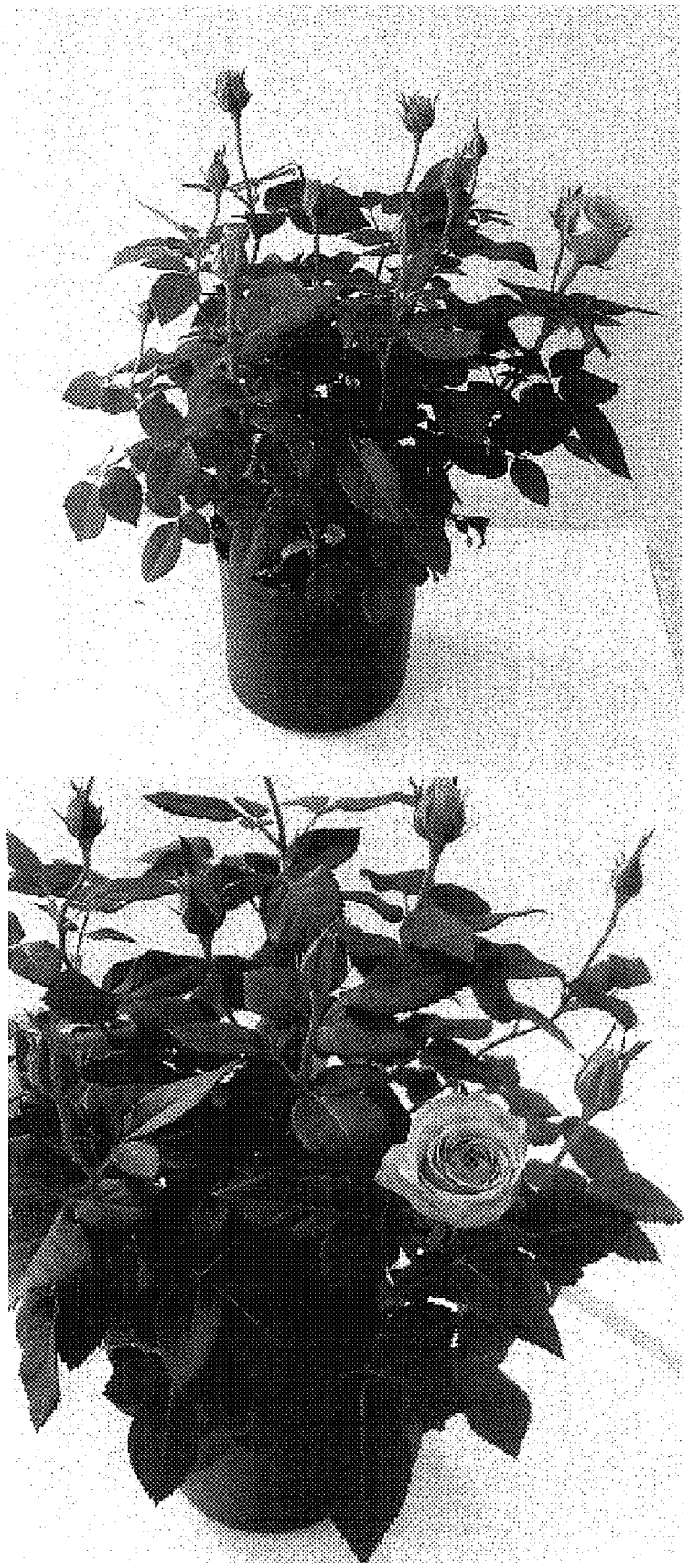

* * * * *